(12) United States Patent
Yoshida et al.

(10) Patent No.: US 9,610,094 B2
(45) Date of Patent: Apr. 4, 2017

(54) METHOD AND APPARATUS FOR ULTRASONIC DIAGNOSIS

(75) Inventors: Tetsuya Yoshida, Tochigi-ken (JP); Yoko Okamura, Tochigi-ken (JP)

(73) Assignees: KABUSHIKI KAISHA TOSHIBA, Tokyo (JP); TOSHIBA MEDICAL SYSTEMS CORPORATION, Otawara-shi (JP)

(*) Notice: Subject to any disclaimer, the term of this patent is extended or adjusted under 35 U.S.C. 154(b) by 1 day.

(21) Appl. No.: 13/098,598

(22) Filed: May 2, 2011

(65) Prior Publication Data

US 2011/0270087 A1 Nov. 3, 2011

(30) Foreign Application Priority Data

Apr. 30, 2010 (JP) ................................. 2010-105423

(51) Int. Cl.

| A61B 19/00 | (2006.01) |
|---|---|
| A61B 17/34 | (2006.01) |
| A61B 8/06 | (2006.01) |
| A61B 8/08 | (2006.01) |
| A61B 8/13 | (2006.01) |
| A61B 8/00 | (2006.01) |
| A61B 18/12 | (2006.01) |
| A61B 90/00 | (2016.01) |

(52) U.S. Cl.
CPC ............ *A61B 17/3403* (2013.01); *A61B 8/06* (2013.01); *A61B 8/0841* (2013.01); *A61B 8/13* (2013.01); *A61B 8/4245* (2013.01); *A61B 8/4444* (2013.01); *A61B 8/461* (2013.01); *A61B 8/463* (2013.01); *A61B 8/5238* (2013.01); *A61B 18/12* (2013.01); *A61B 2017/3413* (2013.01); *A61B 2090/365* (2016.02)

(58) Field of Classification Search
CPC ...................................................... A61B 8/461
USPC ......................................................... 600/443
See application file for complete search history.

(56) References Cited

U.S. PATENT DOCUMENTS

| 5,622,173 A | * | 4/1997 | Bisson et al. ................. 600/459 |
| 5,967,985 A | * | 10/1999 | Hayakawa ........... A61B 8/0833 |
| | | | 600/440 |
| 6,413,217 B1 | * | 7/2002 | Mo .............................. 600/440 |
| 2003/0220541 A1 | * | 11/2003 | Salisbury et al. ............ 600/101 |

(Continued)

FOREIGN PATENT DOCUMENTS

JP    2010-068904    *    4/2010    ............... A61B 8/00

*Primary Examiner* — Patricia Park
(74) *Attorney, Agent, or Firm* — Oblon, McClelland, Maier & Neustadt, L.L.P.

(57) ABSTRACT

An apparatus for ultrasonic diagnosis including a probe configured to transmit ultrasonic waves and to receive reflected ultrasonic waves, an image generator configured to generate an ultrasonic image based on the reflected waves, an image synthesizing unit configured to generate a synthetic image in which a puncture guideline, which indicates a passing line of a puncture needle inserted from a puncture adapter attached to the probe, is superposed on the ultrasonic image, a display area adjusting unit configured to adjust a display area of the synthetic image based on the passing line of the puncture needle, and a display controller configured to display the synthetic image on a monitor based on the display area adjusted by the display area adjusting unit.

3 Claims, 12 Drawing Sheets

(56) References Cited

U.S. PATENT DOCUMENTS

| | | | |
|---|---|---|---|
| 2005/0226593 A1* | 10/2005 | Glassman | H04N 5/765 386/353 |
| 2005/0240104 A1* | 10/2005 | Shim et al. | 600/437 |
| 2008/0044069 A1* | 2/2008 | DuGal | 382/128 |
| 2008/0091101 A1* | 4/2008 | Velusamy | A61B 6/032 600/427 |
| 2008/0186378 A1* | 8/2008 | Shen et al. | 348/65 |
| 2008/0246724 A1* | 10/2008 | Pan et al. | 345/157 |
| 2009/0198094 A1* | 8/2009 | Fenster et al. | 600/3 |
| 2009/0306511 A1* | 12/2009 | Yamagata | 600/447 |
| 2011/0166451 A1* | 7/2011 | Blaivas et al. | 600/439 |

* cited by examiner

FIG.12
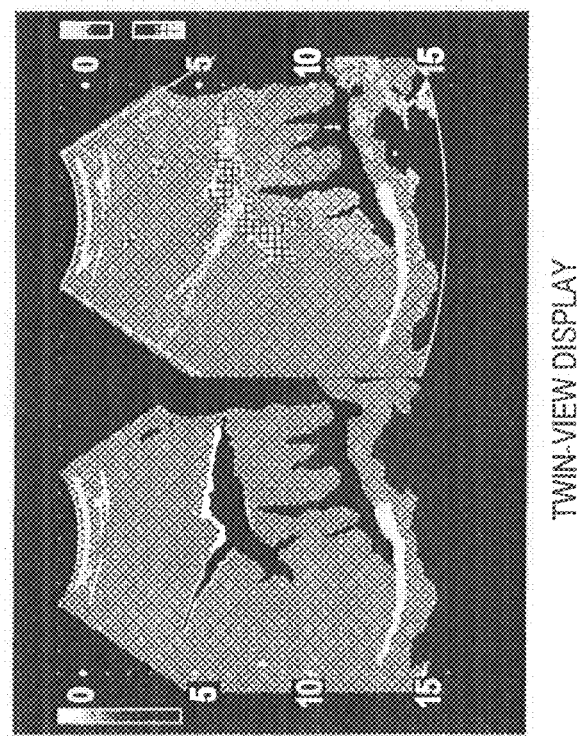
TWIN-VIEW DISPLAY
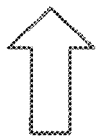
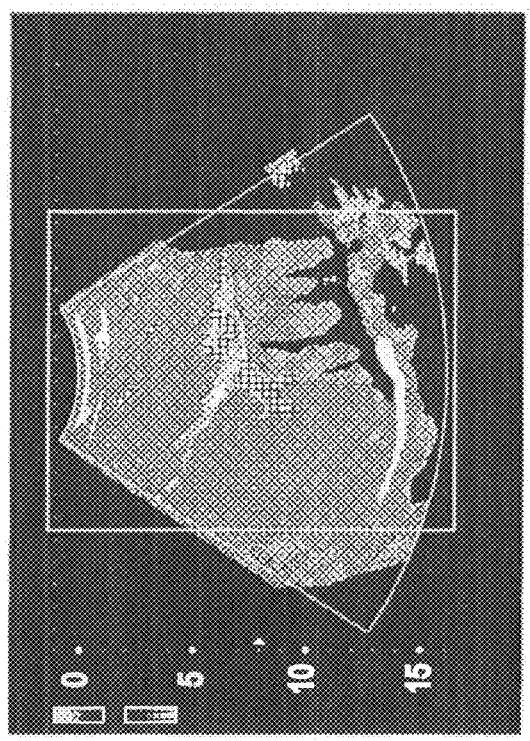
SINGLE DISPLAY

METHOD AND APPARATUS FOR ULTRASONIC DIAGNOSIS

CROSS-REFERENCE TO RELATED APPLICATIONS

This application is based upon and claims the benefit of priority from Japanese Patent Application No. 2010-105423, filed Apr. 30, 2010, the entire contents of which are incorporated herein by reference.

FIELD

Embodiments described herein relate generally to a method and an apparatus for ultrasonic diagnosis, and more particularly to techniques for performing a puncturing operation.

BACKGROUND

In recent years, ultrasonic diagnosis apparatuses have played an important role in contemporary medical treatment, because they are smaller in scale than other medical image diagnosis apparatuses, such as an X-ray diagnosis apparatus, a CT (Computed Tomography) apparatus, and an MRI (Magnetic Resonance Imaging) apparatus, and can display the movement of an object under examination such as the pulsation of a heart or the movement of a fetus in real time with a simple operation of bringing an ultrasonic probe into contact with the body surface of the object. Further, an ultrasonic diagnosis apparatus is free from the influence of exposure to radiation and portable ultrasonic diagnosis devices have been developed. Such ultrasonic diagnosis apparatuses can be easily used in medical locations such as maternity wards or home medical care services.

An ultrasonic diagnosis apparatus can generate and display ultrasonic images in various modes in real time on the basis of reflected ultrasonic waves received by an ultrasonic probe by scanning the same cross-section with ultrasonic waves with different scanning sequences. Specifically, the ultrasonic diagnosis apparatus can generate and display ultrasonic images in various modes, such as a B-mode image, a color Doppler image, a contrast-enhanced image using an ultrasonic contrast agent, and an image in which a special target (for example, a calcified area) is highlighted by a filtering process in real time.

The ultrasonic diagnosis apparatus has a function of displaying ultrasonic images in two modes obtained by imaging the same cross-section in parallel, i.e., a twin-view display. FIG. 12 is a diagram illustrating the twin-view display.

For example, as shown in the left part of FIG. 12, an operator inputs a twin-view display request for a color Doppler image and a B-mode image when the ultrasonic diagnosis apparatus displays only a color Doppler image (single display). In this case, the ultrasonic diagnosis apparatus displays images in two modes with the same scale (display enlargement rate) as the single display. For example, the ultrasonic diagnosis apparatus trims the color Doppler image in the single display by the use of the rectangle indicated in the left part of FIG. 12. As shown in the right part of FIG. 12, the ultrasonic diagnosis apparatus then displays the trimmed color Doppler image and a B-mode image in the same range as the trimmed color Doppler image.

The ultrasonic diagnosis apparatus is widely used for performing a puncturing operation, such as a vital histological examination or a radio frequency ablation (RFA) treatment, because it can display ultrasonic images in real time. For example, when tissue collection is made for the vital histological examination, a doctor punctures a body with a puncture needle and collects the tissue, while checking a target lesion in real time by use of an ultrasonic image. When the RFA is performed, the doctor punctures a lesion site with a puncture needle while checking the target lesion by use of an ultrasonic image in real time, and then emits radio waves from the puncture needle.

In recent years, an attachment, such as a puncture adapter, that can be detachably attached to an ultrasonic probe has been developed so as to allow insertion of a puncture needle at a predetermined angle and position at the time of performing a puncturing operation. An ultrasonic diagnosis apparatus that displays an ultrasonic image along with a line (puncture guideline) through which the puncture needle passes so as to overlap with each other by the use of the information of the puncture adapter has been developed. Accordingly, an operator can determine the position of an ultrasonic probe at the time of inserting a puncture needle on the basis of the positional relation between the puncture guideline and a target site.

The puncturing operation may be performed with reference to an ultrasonic image in one of the above-mentioned different modes, in addition to the B-mode image. For example, when it is necessary to check whether a puncture needle is not inserted into blood vessels, an operator performs the puncturing operation with reference to a color Doppler image. For example, when an operator intends to collect tissue from a suspected site of a liver tumor, the operator performs the puncturing operation with reference to a contrast-enhanced image. When the operator intends to collect tissue from a calcified site, the operator performs the puncturing operation with reference to an image in a calcification-highlighted display mode.

Accordingly, an operator typically performs a puncturing operation with reference to a B-mode image and an ultrasonic image in another mode through the use of a twin-view display (parallel display).

BRIEF DESCRIPTION OF THE DRAWINGS

FIG. 12 is a diagram illustrating the twin-view display.

DETAILED DESCRIPTION

Hereinafter, an ultrasonic diagnosis apparatus according to exemplary embodiments will be described in detail with reference to the accompanying drawings.

First Embodiment

Figure 1:
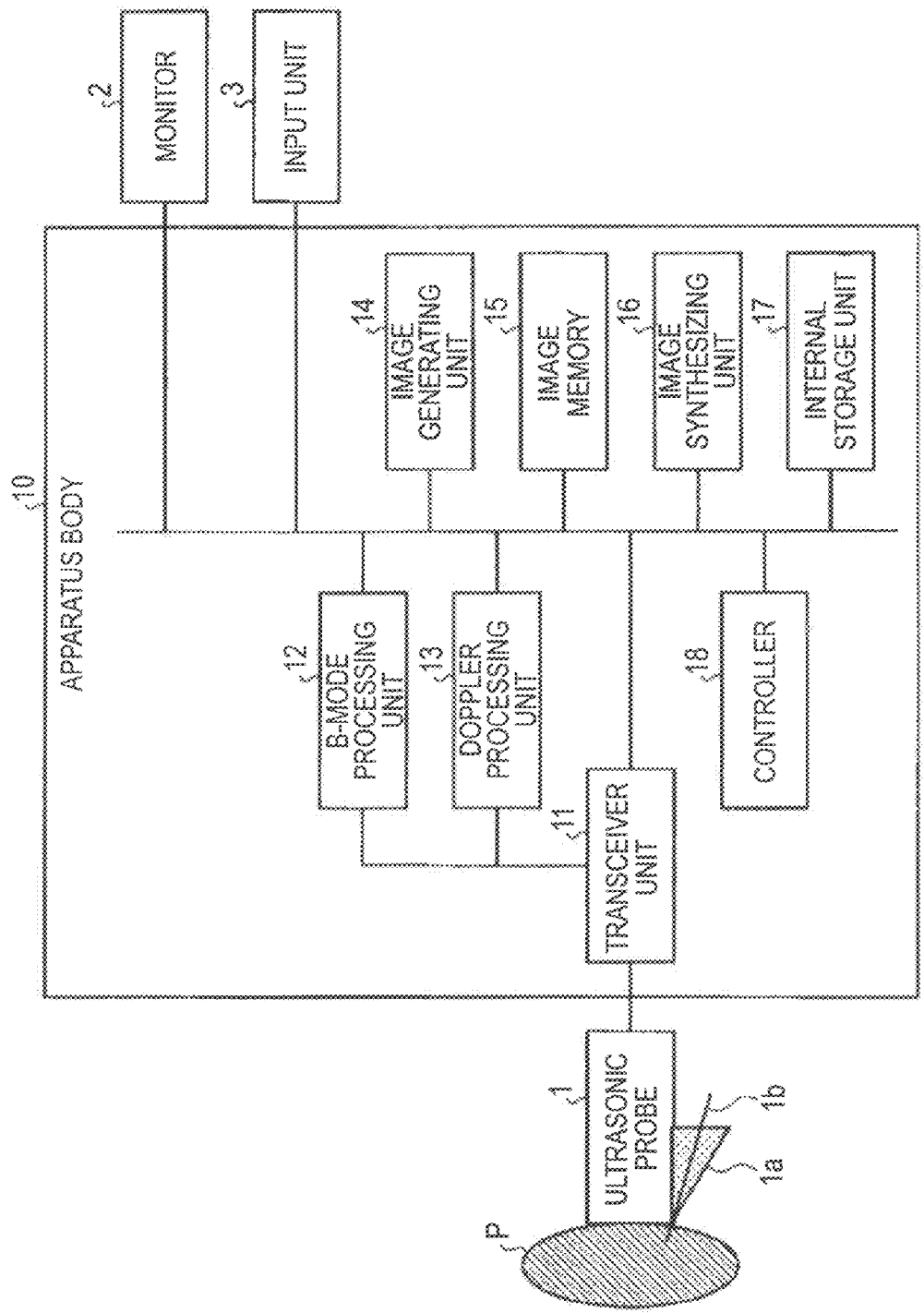
FIG. 1 is a diagram illustrating the configuration of the ultrasonic diagnosis apparatus according to a first embodiment.

First, the configuration of an ultrasonic diagnosis apparatus according to a first embodiment will be described. FIG. 1 is a diagram illustrating the configuration of the ultrasonic diagnosis apparatus according to the first embodiment. As shown in FIG. 1, the ultrasonic diagnosis apparatus according to the first embodiment includes an ultrasonic probe 1, a monitor 2, an input unit 3, and an apparatus body 10.

The ultrasonic probe 1 includes plural piezoelectric vibrators. The plural piezoelectric vibrators generate ultrasonic waves on the basis of a drive signal supplied from a transceiver unit 11 of the apparatus body 10 (to be described later), and receive and convert reflected waves from a test object P into electrical signals. The ultrasonic probe 1 includes an alignment layer disposed in the piezoelectric vibrators and a backing material used to prevent the propagation of ultrasonic waves from the piezoelectric vibrators to the rear side.

When ultrasonic waves are transmitted from the ultrasonic probe 1 to the test object P, the transmitted ultrasonic waves are sequentially reflected by acoustic impedance discontinuities in the internal body tissue of the test object P and are received as reflected wave signals by the piezoelectric vibrators of the ultrasonic probe 1. The amplitudes of the received, reflected wave signals depend on the acoustic impedance differences in the discontinuities from which the ultrasonic waves are reflected. When the transmitted ultrasonic pulses are reflected from a moving blood flow or the surface of a cardiac wall, the reflected wave signals are subjected to a frequency shift due to the Doppler effect, depending on the velocity component of a moving body in the ultrasonic transmission direction.

A puncture adapter 1a is attached to the ultrasonic probe 1 according to the first embodiment, so that an operator can perform a puncturing operation for vital histological examination or radio frequency ablation (RFA) treatment while viewing ultrasonic images. A puncture needle 1b is attached to the puncture adapter 1a. The operator inserts the puncture needle 1b attached to the puncture adapter 1a to a target site of the test object P while viewing the ultrasonic images.

In the first embodiment, it is assumed that the ultrasonic probe 1 is a linear scanning type that transmits the ultrasonic waves linearly.

The input unit 3 includes, for example, a mouse, a keyboard, buttons, a panel switch, a touch command screen, a foot switch, and a track ball, receives various setting requests from an operator of the ultrasonic diagnosis apparatus, and transmits the received setting requests to the apparatus body 10. Specifically, the input unit 3 receives a display mode changing request. More specifically, the input unit 3 receives a "single-view display" request for displaying an ultrasonic image in one mode from the operator, or receives a "twin-view display" request for displaying ultrasonic images in two modes in parallel from the operator. The input unit 3 receives a setting request for a puncture angle (to be described later) of the puncture adapter 1a attached to the ultrasonic probe 1 from the operator.

The monitor 2 displays a GUI (Graphical User Interface) for allowing the operator of the ultrasonic diagnosis apparatus to input various setting requests using the input unit 3 and displays an ultrasonic image generated by the apparatus body 10.

The apparatus body 10 serves to generate an ultrasonic image on the basis of the reflected waves received by the ultrasonic probe 1 and includes a transceiver unit 11, a B-mode processing unit 12, a Doppler processing unit 13, an image generator 14, an image memory 15, an image synthesizing unit 16, an internal storage unit 17, and a controller 18, as shown in FIG. 1.

The transceiver unit 11 includes a trigger generator circuit, a delay circuit, and a pulsar circuit, and supplies a drive signal to the ultrasonic probe 1. The pulsar circuit repeatedly generates a rated pulse for forming transmission ultrasonic waves at a predetermined rated frequency. The delay circuit focuses ultrasonic waves generated from the ultrasonic probe 1 in a beam shape and provides a delay time for each piezoelectric vibrator necessary for determining transmission directivity to the rated pulses generated by the pulsar circuit. The trigger generator circuit applies the drive signal (drive pulses) to the ultrasonic probe 1 at times based on the rated pulses. That is, the delay circuit adjusts the transmission direction from the piezoelectric vibrator plane by changing the delay time given to the rated pulses.

The transceiver unit 11 also includes an amplifier circuit, an A/D converter, and an adder, and performs various processes on the reflected wave signal received by the ultrasonic probe 1 to generate reflected wave data. The amplifier circuit amplifies the reflected wave signal for each channel and performs a gain correcting process. The A/D converter converts the reflected wave signal with the corrected gain in an A/D conversion manner and provides the delay time necessary for determining reception directivity. The adder performs an adding process on the reflected wave signals processed by the A/D converter to generate the reflected wave data. By the adding process of the adder, the reflected component in the direction corresponding to the reception directivity of the reflected wave signals is highlighted.

In this way, the transceiver unit 11 controls the transmission directivity and the reception directivity in transmitting and receiving ultrasonic waves. The transceiver unit 11 has a function of instantaneously changing delay information, a transmission frequency, a transmission drive voltage, the number of aperture elements under the control of the controller 18, to be described later. The transceiver unit 11 can transmit and receive different waveforms every frame or rate.

The B-mode processing unit 12 receives the reflected wave data, which is processed reflected wave signals having been subjected to the gain correcting process, the A/D conversion process, and the adding process, from the transceiver unit 11 and generates B-mode data, in which the signal intensity is expressed by brightness, by performing processes such as logarithmic amplification and envelope detection on the received data.

Here, the B-mode processing unit 12 can change the frequency band to be imaged by changing the detected frequency. The B-mode processing unit 12 can perform the detection process using two detection frequencies on portions of received data in parallel.

By using the processing of the B-mode processing unit 12, the reflected wave data reflected from an ultrasonic contrast agent (microbubbles) flowing in a region of interest and the reflected wave data reflected from a tissue existing in the region of interest can be separated from a portion of received data from the region of interest of the test object P into which the contrast agent has been injected. The image generating unit 14 (to be described later) can generate a contrast-enhanced image obtained by imaging flowing bubbles with high sensitivity and a tissue image obtained by imaging a tissue for observing the shape of the tissue.

The Doppler processing unit 13 analyzes velocity information from the reflected wave data received from the transceiver unit 11 by frequency, extracts echo components of a blood flow, a tissue, and a contrast agent due to the Doppler effect, and generates Doppler data obtained by extracting moving object information, such as average velocity, variance, and power, from plural points.

The image generating unit 14 generates a B-mode image in which the intensity of the reflected wave is expressed by brightness on the basis of the B-mode data generated by the B-mode processing unit 12 and a color Doppler image, such as an average velocity image, a variance image, a power image, or a combined image thereof representing the information of a moving object, on the basis of the Doppler data generated by the Doppler processing unit 13 as ultrasonic images.

When the contrast imaging is performed on the test object P into which a contrast agent has been injected, the image generating unit 14 generates a contrast-enhanced image or a tissue image from the signals acquired by the B-mode processing unit 12. The image generating unit 14 can generate an image in which a specific target (for example, a calcified site) is highlighted by filtering the B-mode data generated by the B-mode processing unit 12.

In this way, by scanning the same cross-section of the test object P with the ultrasonic waves in different scanning sequences, the image generating unit 14 generates the ultrasonic images in various modes such as the B-mode image, the color Doppler image, the contrast-enhanced image, and the image in the calcification-highlighted display mode on the basis of the reflected ultrasonic waves received by the use of the ultrasonic probe 1 in real time.

The image generating unit 14 converts (scan-coverts) an ultrasonic scanning signal sequence into a signal sequence of a video format represented by a television and generates an ultrasonic image as a display image.

The internal storage unit 17 stores control programs used to perform an ultrasonic wave transmitting and receiving process, an image process, and a display process or various data such as diagnosis information (for example, patient IDs and doctor's opinions), diagnosis protocols, and various body marks. The internal storage unit 17 may store images stored in the image memory 15 if necessary. The data stored in the internal storage unit 17 can be transmitted to an external peripheral device via an interface circuit (not shown). The internal storage unit 17 according to the first embodiment stores the puncture angle of the puncture needle 1*b*, which is inserted into the test object P from the puncture adapter 1*a* attached to the ultrasonic probe 1. For example, the internal storage unit 17 stores an insertion angle "37 degrees" of the puncture needle 1*b* about the biological body surface of the test object P with which the ultrasonic probe 1 having the puncture adapter 1*a* attached thereto comes in contact as the puncture angle of the puncture adapter 1*a*. The internal storage unit 17 also stores a display size of the monitor 2.

Figure 2:
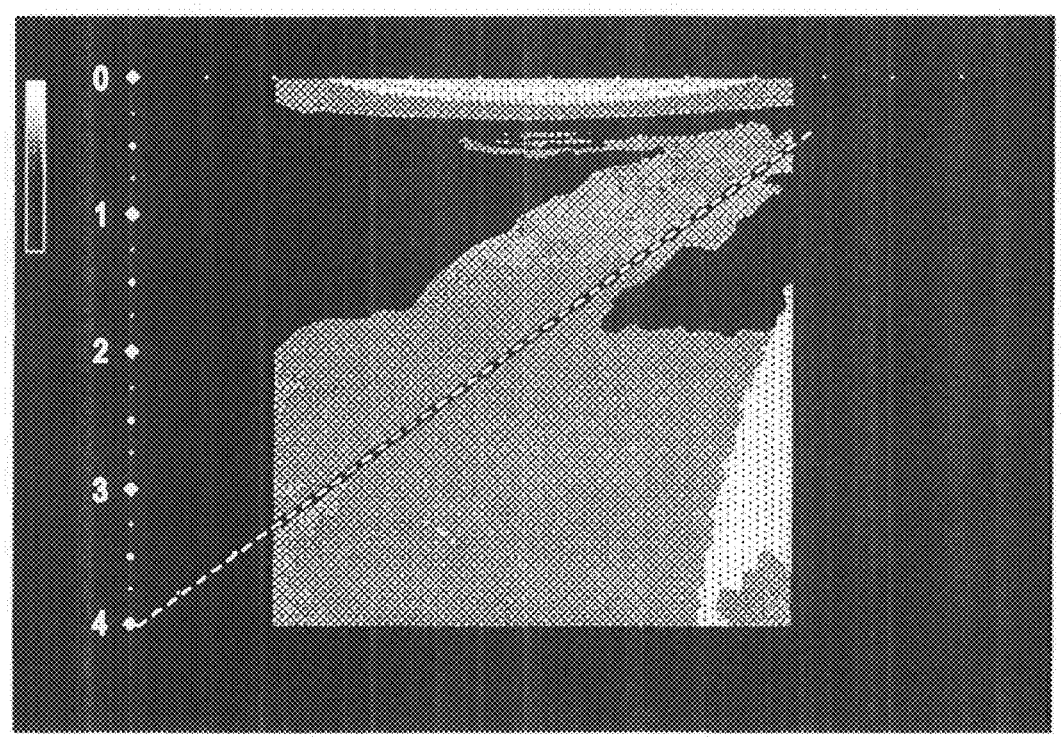
FIG. 2 is a diagram illustrating an operation of the image synthesizing unit.

The image synthesizing unit 16 synthesizes the ultrasonic image generated by the image generator 14 with text information of various parameters, scales, and body marks and outputs the resultant image as a video signal to the monitor 2. Here, the image synthesizing unit 16 according to the first embodiment generates a synthetic image in which a puncture guideline, which is a passing line of the puncture needle 1*b* inserted from the puncture adapter 1*a* attached to the ultrasonic probe 1, is superposed on the ultrasonic image output to the monitor 2. Specifically, the image synthesizing unit 16 acquires the puncture angle of the puncture adapter 1*a* stored in advance in the internal storage unit 17 and superposes the puncture guideline on the ultrasonic image. FIG. 2 is a diagram illustrating an image generated by the image synthesizing unit.

For example, the image synthesizing unit 16 acquires the puncture angle "37 degrees" of the puncture adapter 1*a* from the internal storage unit 17 and generates a synthetic image in which a dotted puncture guideline is superposed on the B-mode image, as shown in FIG. 2.

The image memory 15 is a memory storing the ultrasonic image generated by the image generating unit 14 or the synthetic image synthesized by the image synthesizing unit 16.

The controller 18 controls all the processes of the ultrasonic diagnosis apparatus. Specifically, the controller 18 controls the processes of the transceiver unit 11, the B-mode processing unit 12, the Doppler processing unit 13, and the image generator 14 on the basis of various setting requests input from the operator via the input unit 3 or various control programs and various data read from the internal storage unit 17, and controls the monitor 2 to display the ultrasonic image or the synthetic image stored in the image memory 15.

Hitherto, the configuration of the ultrasonic diagnosis apparatus according to the first embodiment of the invention is described. By means of this configuration, the ultrasonic diagnosis apparatus according to the first embodiment generates ultrasonic images in two modes that are obtained by imaging the biological tissue of the test object P into which the puncture needle 1*b* is inserted. The ultrasonic diagnosis apparatus according to the first embodiment generates two synthetic images in which the puncture guideline is superposed on the ultrasonic images in two modes and performs the display control of the synthetic images.

Specifically, when a request to display the synthetic images in two modes in parallel (twin-view display) is input via the input unit 3 from the operator, the ultrasonic diagnosis apparatus according to the first embodiment performs the display control process of the controller 18 to be described below in detail, whereby the visibility of the puncture guideline can be guaranteed in spite of the parallel display of two ultrasonic images (synthetic images).

It is assumed in the following description that when a B-mode image (hereinafter, referred to as a B-mode synthetic image) on which the puncture guideline is superposed is being singly displayed on the monitor 2, the "twin-view display" request to display the B-mode synthetic image and a color Doppler image (hereinafter, referred to as color Doppler synthetic image) on which the puncture guideline is superposed in parallel is input via the input unit 3. Here, the first embodiment may be applied to a case in which the synthetic images of the ultrasonic images in different modes, such as the contrast-enhanced image or the image in the calcification-highlighted display mode, should be displayed in parallel.

Figure 3:
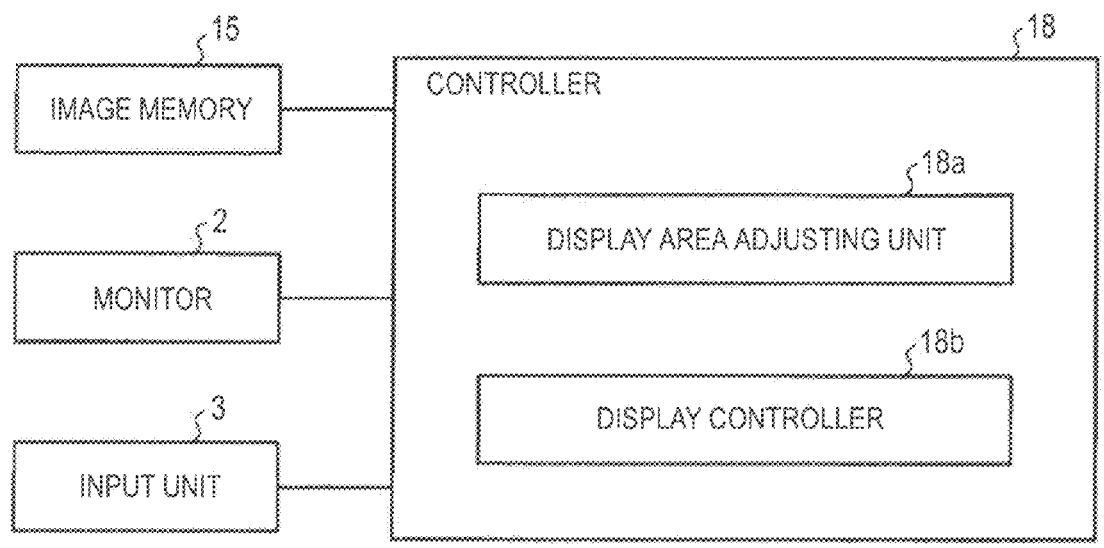
FIG. 3 is a diagram illustrating the configuration of the controller 18 according to the first embodiment.

FIG. 3 is a diagram illustrating the configuration of the controller 18 according to the first embodiment. As shown in FIG. 3, the controller 18 according to the first embodiment includes a display area adjusting unit 18a and a display controller 18b.

The display area adjusting unit 18a performs the following processes when the request to display the synthetic images in two modes in parallel (twin-view display request) is input via the input unit 3 from the operator. That is, the display area adjusting unit 18a reads the synthetic images in two modes from the image memory 15. The display area adjusting unit 18a adjusts the display area for displaying the synthetic images in two modes in parallel so as to include the shallowest part in the passing line of the puncture needle among the areas of the ultrasonic images. Specifically, the display area adjusting unit 18a determines a scanning line passing through the shallowest part out of the scanning lines of the ultrasonic probe 1 that scans the biological body surface with ultrasonic waves in a straight line perpendicular to the biological body surface.

Figure 4:
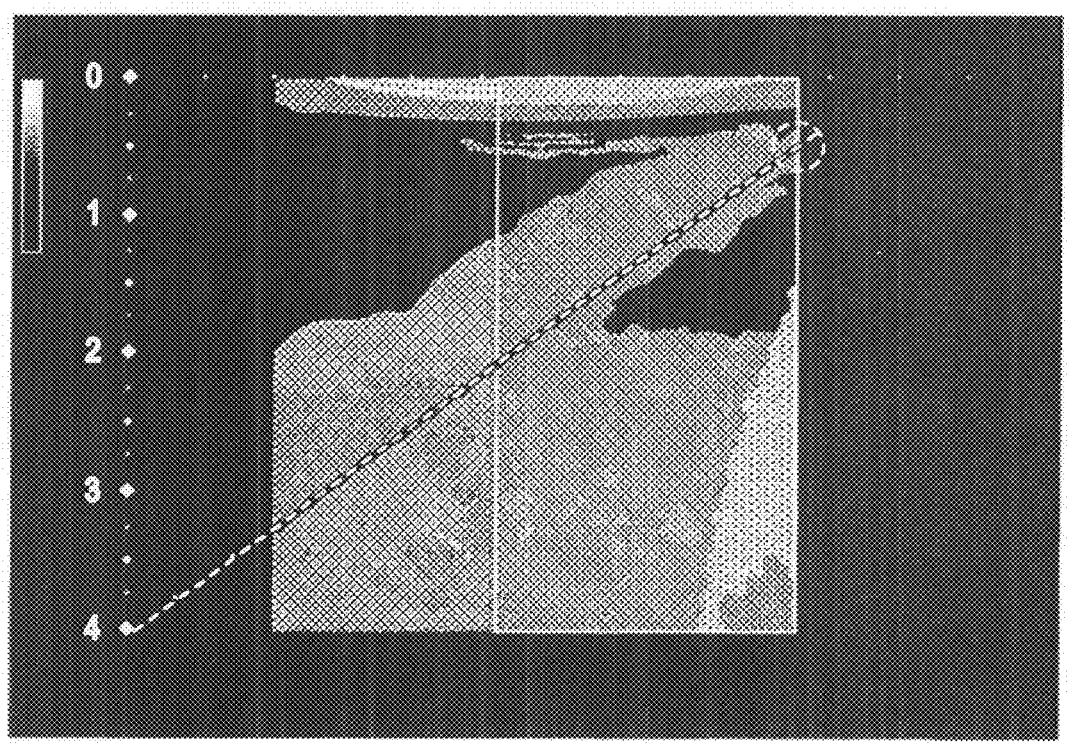
FIG. 4 is a diagram illustrating an operation of the display area adjusting unit according to the first embodiment.

The display area adjusting unit 18a determines, as the display area, a range included in the display size of the monitor 2 at the time of performing the parallel display after including the scanning line passing through the shallowest part. FIG. 4 is a diagram illustrating the operation of the display area adjusting unit according to the first embodiment.

For example, the display area adjusting unit 18a determines the range between the scanning line passing through the shallowest part (see the dotted circle in FIG. 4) in the passing line of the puncture needle and the scanning line located at the position included in the display size of the monitor 2 at the time of performing the parallel display among an area of the ultrasonic image as the display area (see the rectangle in FIG. 4) of the B-mode synthetic image. By the same process, the display area adjusting unit 18a adjusts the display area of the color Doppler synthetic image. The display area adjusting unit 18a acquires the display size of the monitor 2 from the internal storage unit 17.

Figure 5:
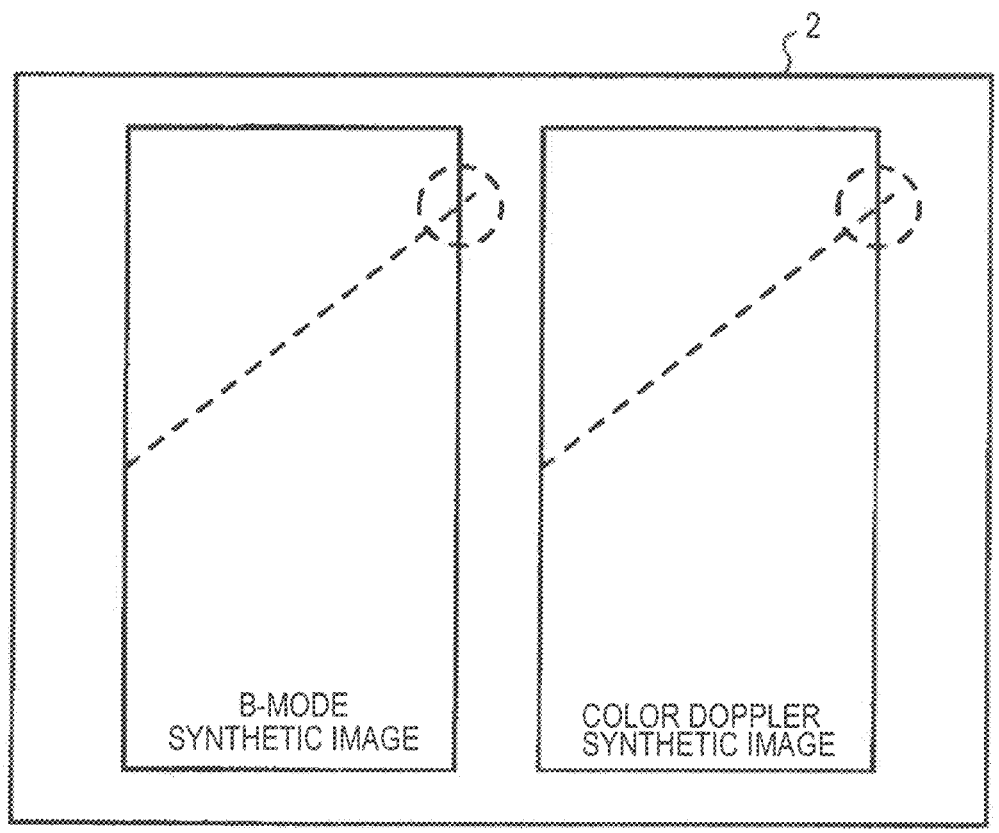
FIG. 5 is a diagram illustrating an operation of the display controller according to the first embodiment.

Referring to FIG. 3 again, the display controller 18b controls the monitor 2 to display two synthetic images in parallel in the display areas adjusted by the display area adjusting unit 18a. FIG. 5 is a diagram illustrating an operation of the display controller according to the first embodiment.

For example, as shown in FIG. 5, the display controller 18b displays the B-mode synthetic image and the color Doppler synthetic image on the monitor 2 in parallel by the use of the display areas including the shallowest part in the passing line of the puncture needle among the areas of the ultrasonic images. Under this control, the monitor 2 displays the synthetic images in two modes in which the shallow part of the puncture guideline is clearly viewed in real time during the puncturing operation.

Figure 6:
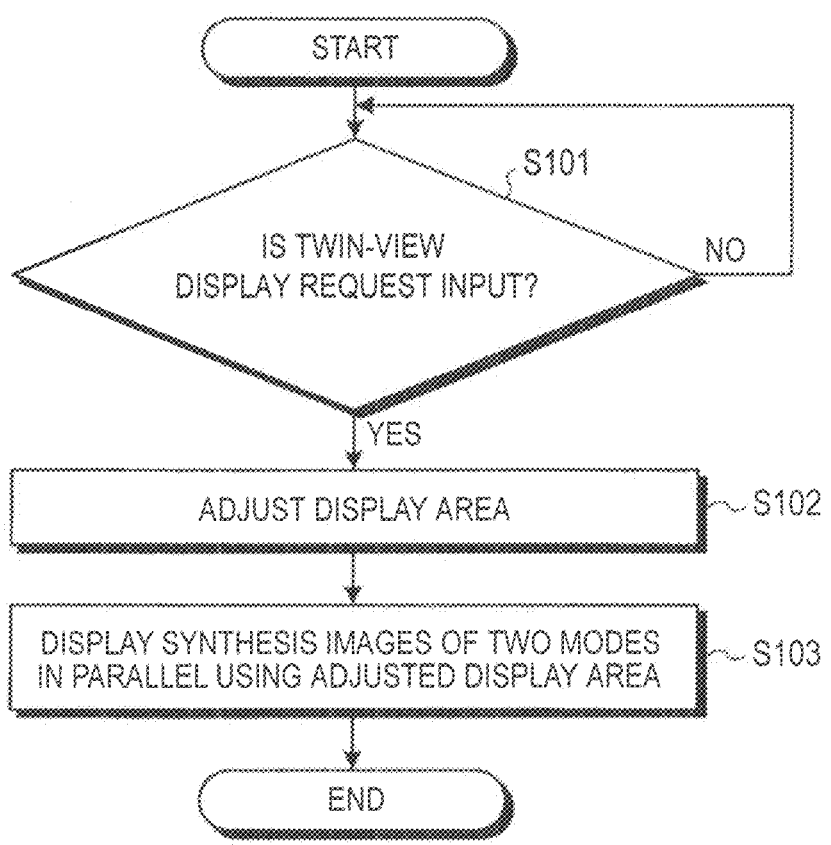
FIG. 6 is a flow chart illustrating a process executed by the ultrasonic diagnosis apparatus according to the first embodiment.

The processes of the ultrasonic diagnosis apparatus according to the first embodiment will be described with reference to FIG. 6. FIG. 6 is a flowchart illustrating the flow of a process performed by the ultrasonic diagnosis apparatus according to the first embodiment.

As shown in FIG. 6, the ultrasonic diagnosis apparatus according to the first embodiment determines whether a twin-view display request to display synthetic images in two modes in parallel is input from the operator (step S101). Here, when it is determined that the twin-view display request is not input (NO in step S101), the ultrasonic diagnosis apparatus remains in a standby state.

On the other hand, when it is determined that the twin-view display request is input (YES in step S101), the display area adjusting unit 18a adjusts the display area for displaying two synthetic images generated by the image synthesizing unit 16 in parallel, so as to include the shallowest part in the passing line of the puncture needle among the areas of the ultrasonic images (step S102). The display controller 18b controls the monitor 2 to display the synthetic images in two modes in parallel by the use of the display areas adjusted by the display area adjusting unit 18a (step S103) and the process ends. After step S103, the display controller 18b controls the monitor 2 to display the synthetic images in two modes, which are sequentially generated, in parallel in real time by the use of the display areas adjusted by the display area adjusting unit 18a.

As described above, in the first embodiment, the image generating unit 14 generates the ultrasonic images in two modes on the basis of the reflected ultrasonic waves received by the ultrasonic probe 1. The image synthesizing unit 16 generates two synthetic images in which the puncture guideline, which is the passing line of the puncture needle 1b inserted from the puncture adapter 1a attached to the ultrasonic probe 1, is superposed on the ultrasonic images in two modes. When the twin-view display request is input via the input unit 3, the display area adjusting unit 18a reads the synthetic images in two modes from the image memory 15. The display area adjusting unit 18a adjusts the display area for displaying the synthetic images in two modes in parallel so as to include the shallowest part in the passing line of the puncture needle among the areas of the ultrasonic images. The display controller 18b controls the monitor 2 to display two synthetic images in parallel by the use of the display areas adjusted by the display area adjusting unit 18a.

Here, in a typical twin-view display, both ends of an image are trimmed out to display the image in half the display area of the monitor 2 so as not to change the depth of view field or the display scale in a single-view display. Particularly, a B-mode image and a color Doppler image are displayed in the twin-view display, for example, in order to check whether any blood vessel exists in the puncture guideline at the time of performing a puncturing operation. However, in the typical twin-view display, the area in which the puncture needle 1b passes through a shallow part of a biological tissue is trimmed out.

On the other hand, in the first embodiment, since the shallowest part of the biological tissue is clearly displayed in the adjusted display area, it is possible to avoid the area of the synthetic image in which the puncture needle 1b passes through the shallow part of the biological tissue from being trimmed out preventing observation of the shallow part of the biological tissue. Therefore, according to the first embodiment, even when two ultrasonic images (synthetic images) are displayed in parallel, it is possible to guarantee the visibility of the puncture guideline.

The display area adjusting process performed by the display area adjusting unit 18a when the ultrasonic probe 1 applies the ultrasonic waves in a linear shape perpendicular to the biological body surface was described above. Here, when the ultrasonic probe applies the ultrasonic waves in a direction not perpendicular to the biological body surface, the display area adjusting process to be described below is performed.

Figure 7A:
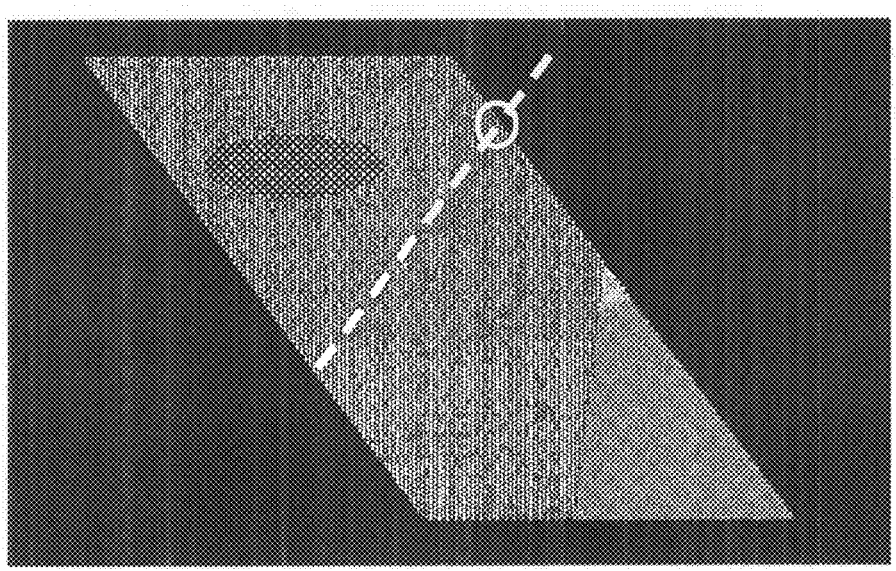
FIGS. 7A and 7B are diagrams illustrating Modification 1 of the display area adjusting process performed by the display area adjusting unit according to the first embodiment.
Figure 7B:
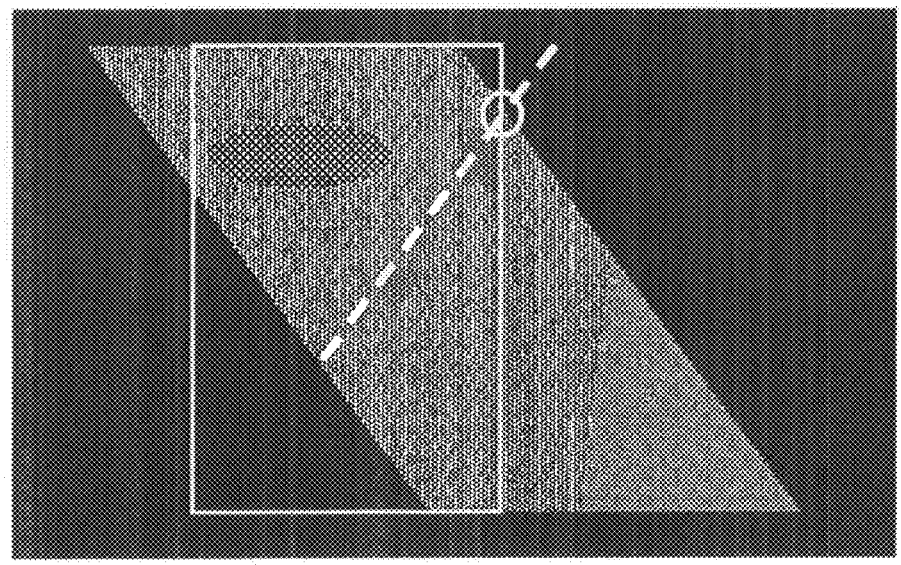

FIGS. 7A and 7B are diagrams illustrating Modification 1 of the display area adjusting process performed by the display area adjusting unit according to the first embodiment. In order to reduce the area that is not imaged among the areas of the biological tissue into which the puncture needle is inserted as much as possible, the direction of the scanning line may be changed to approach the puncture needle, as shown in FIGS. 7A and 7B. As a result, the ultrasonic images of a parallelogram shape are acquired, as shown in FIGS. 7A and 7B, but trapezoidal ultrasonic images may be acquired. In this case, this modification can be applied similarly.

First, the display area adjusting unit 18*a* recognizes the shallowest part (see the dotted circle in FIG. 7A) in the passing line of the puncture needle among the area of the ultrasonic image shown in FIG. 7A. The range included in the display size of the monitor 2 at the time of performing the parallel display after including the scanning line passing through the shallowest part is determined as the display area (see the rectangle in FIG. 7B) of the B-mode synthetic image. By the same process, the display area adjusting unit 18*a* also adjusts the display area of the color Doppler synthetic image.

By these processes, when the ultrasonic waves are applied in a direction not perpendicular to the biological body surface, the condition of the biological tissue close to the shallowest part of the test object P in the insertion path of the puncture needle 1*b* can be displayed as two ultrasonic images along with the puncture guideline. Since the wide area in the insertion direction expressed by the puncture guideline is displayed, it is possible to automatically adjust the display area with the most efficient display condition from the shallow part to the deep part. Therefore, according to Modification 1, even when two ultrasonic images (synthetic images) are displayed in parallel, it is possible to guarantee the visibility of the puncture guideline.

The display area adjusting process performed by the display area adjusting unit 18*a* when the ultrasonic probe 1 is a linear scanning type probe applying ultrasonic waves in a line shape has been described above. Here, when the ultrasonic probe 1 is a convex probe or a sector probe applying ultrasonic waves in a fan shape, the display area adjusting unit 18*a* performs the following display area adjusting process.

Figure 8A:
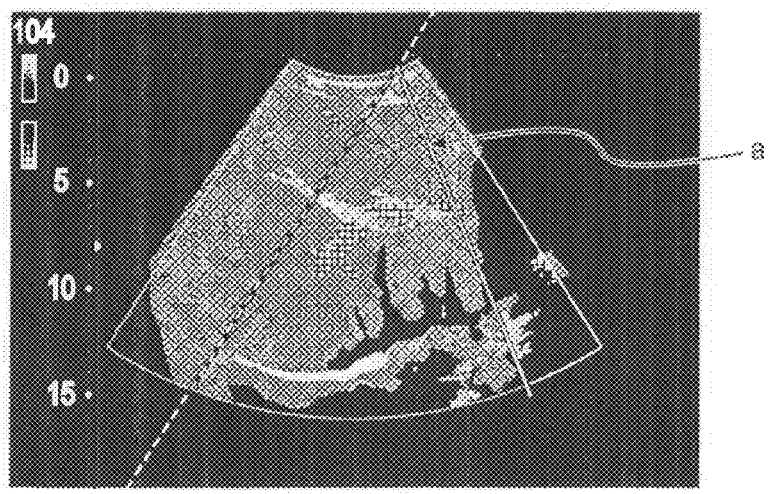
FIGS. 8A to 8C are diagrams illustrating Modification 2 of the display area adjusting process performed by the display area adjusting unit according to the first embodiment.
Figure 8B:
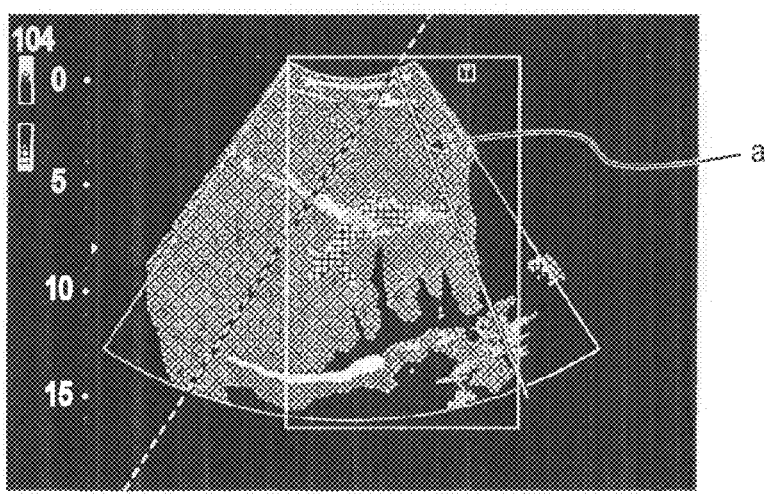
Figure 8C:
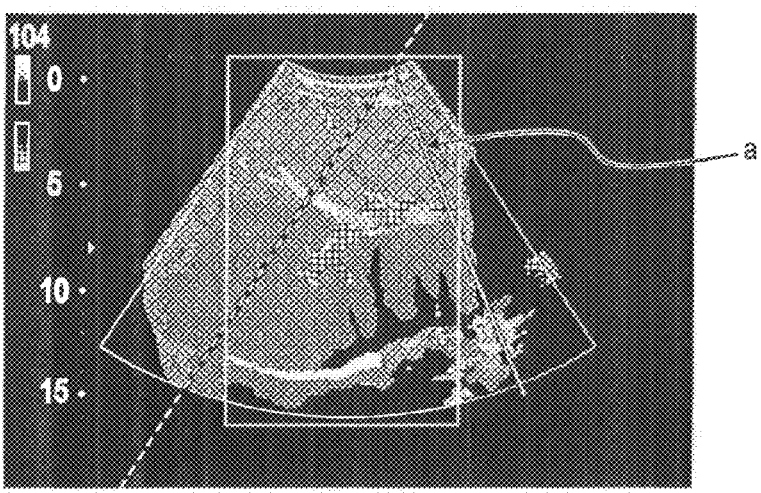

FIGS. 8A to 8C are diagrams illustrating Modification 2 of the display area adjusting process performed by the display area adjusting unit according to the first embodiment.

First, the display area adjusting unit 18*a* determines a scanning line "a" of ultrasonic waves transmitted from the intersection between the puncture guideline and the contact surface of the ultrasonic probe, as shown in FIG. 8A. The display area adjusting unit 18*a* adjusts the display area so as to include the whole determined scanning line, as shown in FIG. 8B. Alternatively, the display area adjusting unit 18*a* adjusts the display area so as to include a part of the determined scanning line, as shown in FIG. 8C. In the example shown in FIG. 8C, the display area is adjusted to include the half scanning line close to the shallow part of the puncture guideline among the determined scanning lines.

By this process, when the ultrasonic waves are applied in the fan shape, the condition of the biological tissue close to the shallowest part of the test object P in the insertion path of the puncture needle 1*b* can be displayed as two ultrasonic images along with the puncture guideline. Therefore, according to Modification 2, it is possible to guarantee the visibility of the puncture guideline even when two ultrasonic images (synthetic images) are displayed in parallel.

It has been described above that the B-mode image and the color Doppler image are displayed as two ultrasonic images, but this embodiment is not limited to this example. Regardless of the type of combination of a freeze image, a past image, a harmonic image, a contrast-enhanced image, a transmitted compound image, and an image in the calcification-highlighted display mode, this embodiment can be applied to displaying plural images. Here, the transmitted compound image is a part of an image obtained by synthesizing plural pieces of data acquired by changing the ultrasonic transmission direction variously.

Second Embodiment

Figure 9:
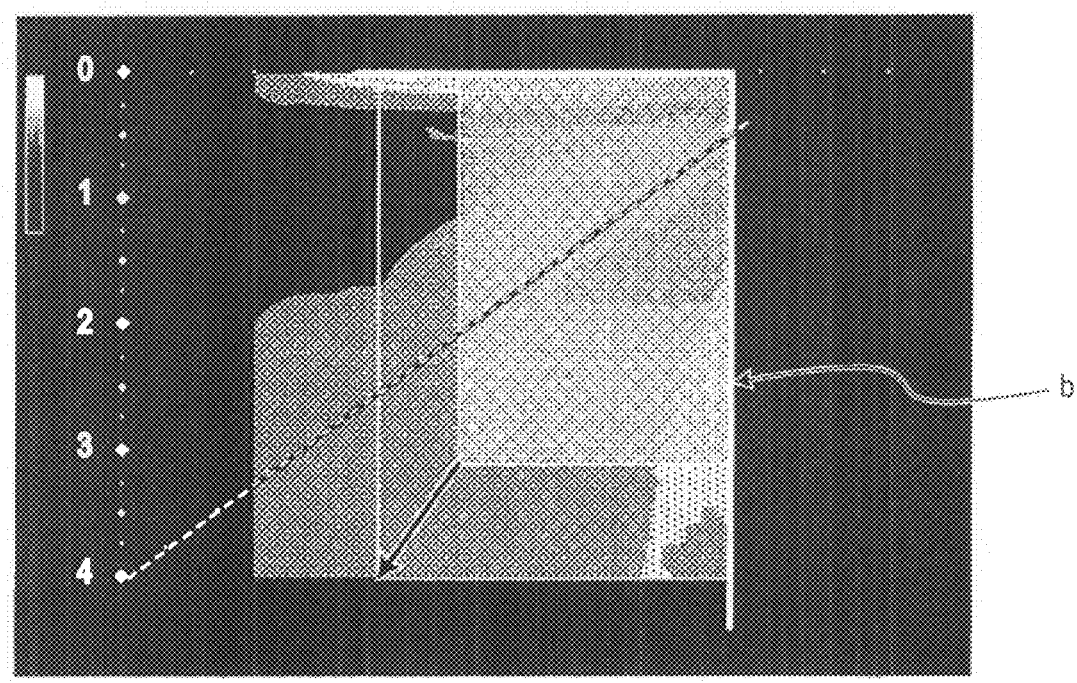
FIG. 9 is a diagram illustrating an operation of a display area adjusting unit according to the second embodiment.
Figure 10:
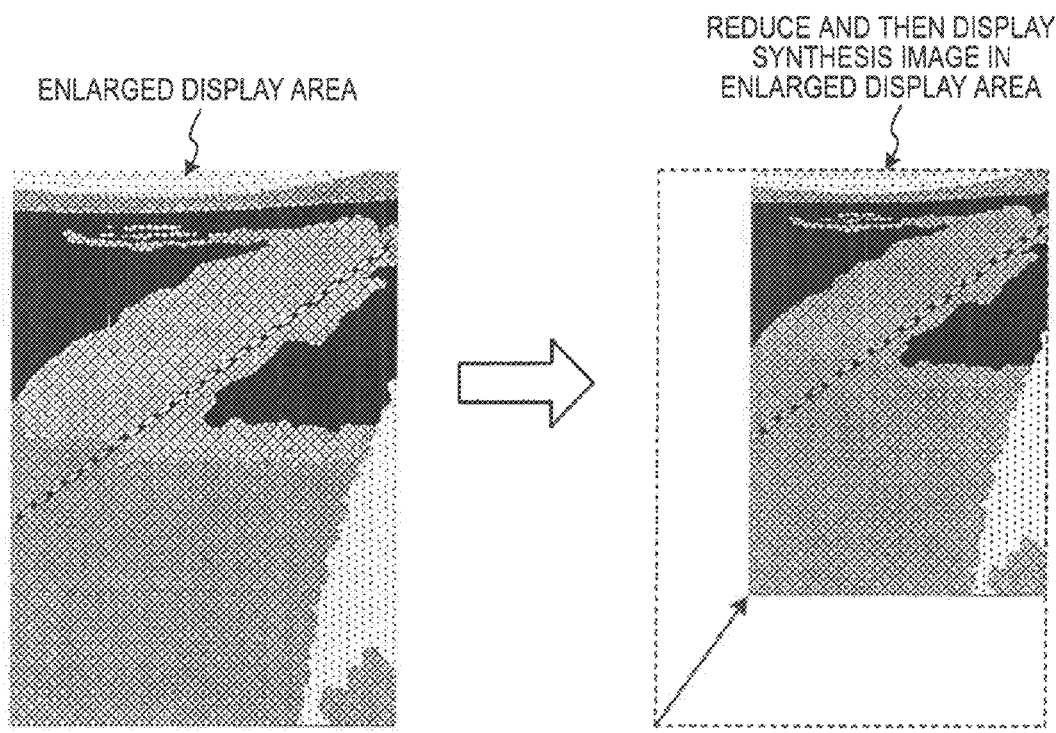
FIG. 10 is a diagram illustrating an operation of a display controller according to the second embodiment.

In a second embodiment of the invention, an example where the display area is re-adjusted will be described with reference to FIGS. 9 and 10. FIG. 9 is a diagram illustrating the operation of a display area adjusting unit according to the second embodiment. FIG. 10 is a diagram illustrating the operation of a display controller according to the second embodiment.

A controller 18 according to the second embodiment has the same configuration as the controller 18 according to the first embodiment described in the first embodiment, but is different from the controller according to the first embodiment in details of the processes performed by the display area adjusting unit 18*a* and the display controller 18*b*. The different details will be described.

First, when an operator referring to synthetic images in two modes displayed in parallel intends to enlarge the display area, the operator inputs a desired enlargement rate, for example, by operating an adjusting knob of the input unit 3. In the second embodiment, a case where a display area enlargement request is input at the time of displaying a B-mode synthetic image and a color Doppler synthetic image in parallel will be described. When the display area enlarging request is input, the display area adjusting unit 18*a* determines a position serving as a reference (reference position) for enlarging the adjusted display area with the input enlargement rate. Specifically, the display area adjusting unit 18*a* according to the second embodiment determines as a reference line "b" a vertical line passing through the shallowest part in the passing line of the puncture needle among the area of the ultrasonic image shown in FIG. 9. Then, as shown in FIG. 9, the display area adjusting unit 18*a* enlarges the display area from the reference line "b" to the deep part of the puncture guideline on the basis of the input enlargement rate.

The display controller 18*b* according to the second embodiment reduces the synthetic images in two modes in the display area enlarged by the display area adjusting unit 18*a* and controls the monitor 2 to display the resultant images in parallel. For example, as shown in FIG. 10, the display controller 18*b* reduces the B-mode synthetic image in the enlarged display area to the non-enlarged size or to half the display size of the monitor 2 and then displays the resultant image on the monitor 2. Similarly, the display controller 18*b* reduces the color Doppler synthetic image in the enlarged display area to the non-enlarged size or to half the display size of the monitor 2 and then displays the resultant image on the monitor 2. As a result, the area of the synthetic images referred to by the operator is enlarged with the reference line "b" as a border. That is, the display area adjusting unit 18*a* enlarges the display area using the reference line "b" as a reference so as not to change the border of the image in the single-view display. As a result, the operator can easily identify the position of the puncture needle when referring to the image at the time of enlarging the range of the referred-to synthetic image. The display controller 18b reduces the synthetic images in the enlarged display areas to display two images together and displays the resultant images.

Figure 11:
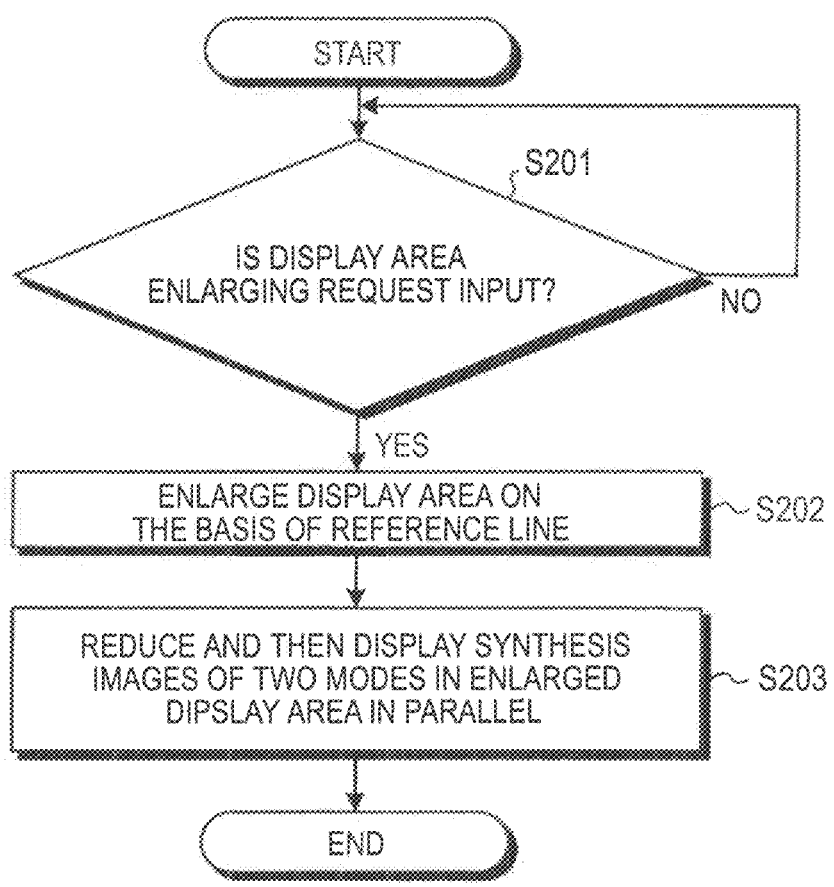
FIG. 11 is a flow chart illustrating a process executed by the ultrasonic diagnosis apparatus according to the second embodiment.

The processes of the ultrasonic diagnosis apparatus according to the second embodiment will be described with reference to FIG. 11. FIG. 11 is a flow chart illustrating a process executed by the ultrasonic diagnosis apparatus according to the second embodiment.

As shown in FIG. 11, the ultrasonic diagnosis apparatus according to the second embodiment determines whether a display area enlarging request is input from the operator (step S201). Here, when it is determined that the display area enlarging request is not input (NO in step S201), the ultrasonic diagnosis apparatus remains in a standby state.

On the other hand, when it is determined that the display area enlarging request is input (YES in step S201), the display area adjusting unit 18a determines a vertical line passing through the shallowest part in the passing line of the puncture needle among the areas of the ultrasonic images as a reference line and enlarges the display area on the basis of the determined reference line (step S202). The display controller 18b reduces the synthetic images in two modes in the display areas enlarged by the display area adjusting unit 18a and controls the monitor 2 to display the synthetic images in parallel (step S203) and the process ends. After step S203, the display controller 18b reduces the synthetic images in two modes sequentially generated by the use of the enlarged display area and then controls the monitor 2 to display the synthetic images in parallel in real time.

As described above, according to the second embodiment, the shallowest part of the biological tissue is clearly displayed even when the display area is enlarged. Therefore, according to the second embodiment, it is possible to guarantee the visibility of the puncture guideline even when two ultrasonic images (synthetic images) are displayed in parallel at the time of performing the puncturing operation while observing the biological tissue in a wide range.

It has been described above that the display area is enlarged, but the second embodiment may be applied to an example where the display area is reduced. Specifically, the display area adjusting unit 18a reduces the display area in a direction directed to the reference line "b" on the basis of an input reduction rate. Then, the display controller 18b enlarges the synthetic images in two modes in the display area reduced by the display area adjusting unit 18a and then controls the monitor 2 to display the resultant images in parallel. For example, the display controller 18b enlarges two synthetic images in the reduced display areas up to the size of the non-reduced display area or up to half the display size of the monitor 2 and then displays the resultant images on the monitor 2. That is, the display area adjusting unit 18a reduces the display area with the reference line "b" as a reference so as not to change the border of the image in the single-view display. As a result, the operator can easily identify the position of the puncture needle when referring to the image at the time of reducing the range of the referred-to synthetic image. Then, the display controller 18b enlarges the synthetic images in the reduced display areas to display two images and display the resultant images. In this modification, the shallowest part of the biological tissue is clearly displayed even when the display area is reduced. Accordingly, in this modification, it is possible to guarantee the visibility of the puncture guideline even when two ultrasonic images (synthetic images) are displayed in parallel at the time of performing the puncturing operation while observing the biological tissue in a narrow range in detail.

Here, the twin-view display has been described in this modification, but this embodiment can be applied to the enlargement and reduction of a display area in a single-view display. In the single-view display, both ends of an ultrasonic image can be displayed the first time, but both ends cannot be displayed when the display area is reduced. In this case, similarly to the above-mentioned modification, the display area can be adjusted with one end as a reference.

The first and second embodiments can be applied to a case where a biological tissue of a test object P being subjected to the puncturing operation by the use of the ultrasonic probe 1 is three-dimensionally scanned in addition to the case where it is two-dimensionally scanned.

The constituent elements of the ultrasonic diagnosis apparatus described and shown in the first and second embodiments are functionally similar, but need not have the same physical configurations as shown in the drawings. That is, specific distributions and integrations of the apparatuses are not limited to ones shown in the drawings, but all or a part thereof may be functionally or physically distributed or integrated in terms of any unit depending on various loads or use conditions. For example, the display area adjusting unit 18a and the display controller 18b may be integrated. All or a part of the processing functions performed by the apparatuses can be embodied by a CPU or programs analyzed and executed by the CPU or by hardware including wired logic circuits.

While certain embodiments have been described, these embodiments have been presented by way of example only, and are not intended to limit the scope of the inventions. Indeed, the novel methods and systems described herein may be embodied in a variety of other forms. Furthermore, various omissions, substitutions, and changes in the form of the methods and systems described herein may be made without departing from the sprit of the inventions. The accompanying claims and their equivalents are intended to cover such forms or modifications as would fall within the scope and spirit of the inventions.

What is claimed is:

1. An apparatus for ultrasonic diagnosis, comprising:
   input circuitry configured to receive, from an operator, a change request for changing a display mode from a single-view mode to a twin-view mode;
   a probe configured to transmit ultrasonic waves to an object and to receive reflected ultrasonic waves from the object along a plurality of scan lines on a cross-section;
   processing circuitry configured to
      generate a two-dimensional ultrasonic image corresponding to the cross-section from reflected wave data based on the reflected waves,
      generate a first synthetic image in which a first puncture guideline, which indicates a passing line of a puncture needle inserted from outside of the object, is superposed on the two-dimensional ultrasonic image,
      cause a monitor to display the first synthetic image in the single-view mode; and
   a memory configured to store a two-dimensional medical image corresponding to the cross-section,
   wherein the processing circuitry is further configured to
      determine a display area to use in the twin-view mode so that an end of the display area includes a shallowest one of intersections of the passing line with the plurality of scan lines, a width of the display area being smaller than a width of the two-dimensional ultrasonic image, generate a second synthetic image in which a second puncture guideline indicating the passing line is superposed on a part of the two-dimensional ultrasonic image corresponding to the display area, generate a third synthetic image in which a third puncture guideline indicating the passing line is superpose on a part of the two-dimensional medical image corresponding to the display area cause the monitor to display the second synthetic image and the third synthetic image side by side in the twin-view mode, the display mode being changed from the single-view mode to the twin-view mode in response to the change request.

2. A method for ultrasonic diagnosis, comprising:

receiving, from an operator, a change request for changing a display mode from a single-view mode to a twin-view mode;

transmitting ultrasonic waves to an object and receiving reflected ultrasonic waves from the object along a plurality of scan lines on a cross-section using an ultrasonic probe;

generating a two-dimensional ultrasonic image corresponding to the cross-section from reflected wave data based on the reflected waves;

generating a first synthetic image in which a first puncture guideline, which indicates a passing line of a puncture needle inserted from outside the object, is superposed on the ultrasonic two-dimensional image;

causing a monitor to display the first synthetic image in the single-view mode;

storing a two-dimensional medical image corresponding to the cross-section;

determining a display area to use in the twin-view mode so that an end of the display area includes a shallowest one of intersections of the passing line with the plurality of scan lines, a width of the display area being smaller than a width of the two-dimensional ultrasonic image;

generating a second synthetic image in which a second puncture guideline indicating the passing line is superposed on a part of the two-dimensional ultrasonic image corresponding to the display area;

generating a third synthetic image in which a third puncture guideline indicating the passing line is superpose on a part of the two-dimensional medical image corresponding to the display area and causing the monitor to display the second synthetic image and the third synthetic image side by side in the twin-view mode, the display mode being changed from the single-view mode to the twin-view mode in response to the change request.

3. The apparatus for ultrasonic diagnosis of claim 1, wherein the plurality of scan lines are arranged in parallel toward an oblique direction, the display area is a rectangular area, and the end of the display area intersects with a right end or a left end scan line at the shallowest one of the intersections.

* * * * *